United States Patent
Cannelli et al.

(10) Patent No.: US 6,728,661 B1
(45) Date of Patent: Apr. 27, 2004

(54) NONDESTRUCTIVE ACOUSTIC METHOD AND DEVICE, FOR THE DETERMINATION OF DETACHMENTS OF MURAL PAINTINGS

(75) Inventors: Giovanni Bosco Cannelli, Rome (IT); Paola Calicchia, Rome (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 98 days.

(21) Appl. No.: 10/018,328

(22) PCT Filed: Jun. 13, 2000

(86) PCT No.: PCT/IT00/00244
§ 371 (c)(1),
(2), (4) Date: Dec. 10, 2001

(87) PCT Pub. No.: WO01/01125
PCT Pub. Date: Jan. 4, 2001

(30) Foreign Application Priority Data

Jun. 25, 1999 (IT) ......................... RM99A0410

(51) Int. Cl.[7] ............................................... G01B 17/00
(52) U.S. Cl. ..................................................... 702/187
(58) Field of Search ..................... 702/189; 600/443, 600/408; 73/602, 67

(56) References Cited

U.S. PATENT DOCUMENTS

| | | | |
|---|---|---|---|
| 4,052,889 A | | 10/1977 | Mucciardi et al. |
| 4,545,250 A | * | 10/1985 | Miwa ........................... 73/602 |
| 4,655,228 A | | 4/1987 | Shimura et al. |
| 5,029,475 A | * | 7/1991 | Kikuchi et al. ............... 73/602 |
| 5,197,019 A | * | 3/1993 | Delon-Martin et al. ..... 600/443 |
| 5,776,063 A | * | 7/1998 | Dittrich et al. ............. 600/408 |

* cited by examiner

*Primary Examiner*—John Barlow
*Assistant Examiner*—Tung S Lau
(74) *Attorney, Agent, or Firm*—Townsend and Townsend and Crew LLP

(57) ABSTRACT

Nondesstrutive acoustic method for the detection of detachments in fresco paintings and generally in mural paintings, which uses as detachment physical indicator, the acoustic absorption coefficient. In the present method, the acoustic source (1) and the detector (2) are placed at a certain distance from the paintings. The use of the "Cepstrum" technique allows to carry out the mearsurements also in presence of background noise, and without knowledge of the value of the direct signal $p_d(t)$, which should be substracted from the detection signal p(t) in order to obtain the reflected signal $p_r(t)$. A microprocessor contained in the device used for the mearsurements, performs the necessary calculations to automatically determine the acoustic energy absorption on predetermined points of the painting surface. By means of an image processing of the so obtained values, bidimensional and tridimensional acoustic images are formed for representing the detachments or separation zones of the painting.

10 Claims, 3 Drawing Sheets

FIG. 4
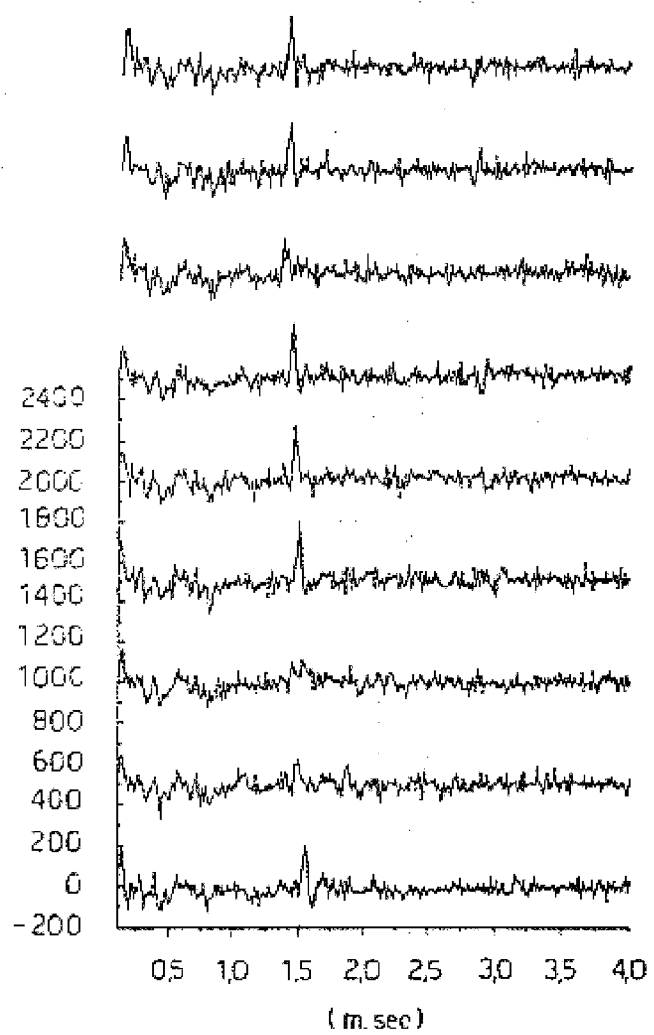
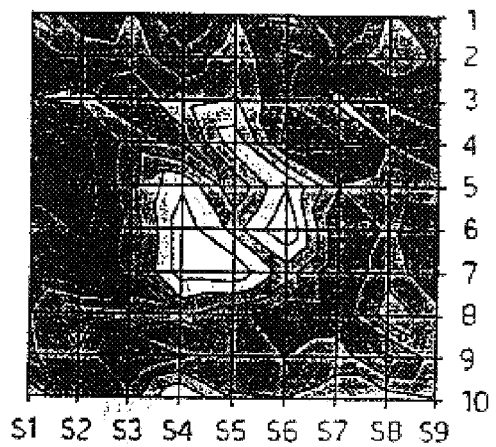
FIG. 8
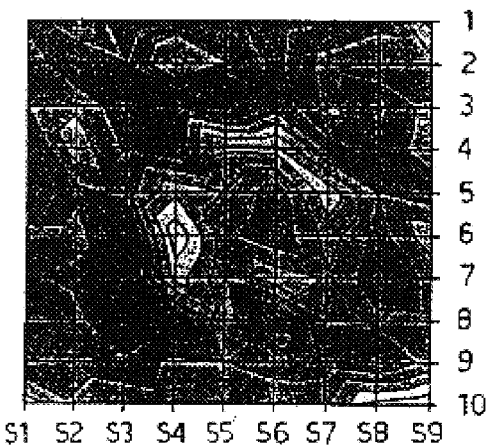
FIG. 9

NONDESTRUCTIVE ACOUSTIC METHOD AND DEVICE, FOR THE DETERMINATION OF DETACHMENTS OF MURAL PAINTINGS

TECHNICAL FIELD

The present invention relates to a method and device suited to obtain a map (bi-dimensional graphic representation) of the extension and the amount of detachments (separation zones) of frescos and generally of mural paintings, in order to estimate the damage caused by environmental conditions (e.g. temperature fluctuations, humidity) to such works of art. Specifically, the present invention concerns a noninvasive or nondestructive method and device for analysing the separation zones, that is, such as to avoid damage to a work of art.

BACKGROUND ART

The research related to the detection and determination of the amount of detachment of the separation zones in frescos is one of the most urgent and difficult problems in the field of conservation and restoration of works of art (see Danti C., Matteini M., Moles, Le pitture murali, Tecniche, Problemi, Conservazione. Centro di Edit., Firenze, 1990). The need to deal with such a problem in a systematic and scientifically valid way is felt even more if we consider that the presence of frescos in the Italian artistic patrimony is very remarkable, both having regard to the number of works and to the value of these masterpieces which are unique in their kind. To better define the problem we are dealing with, it is useful to briefly recall the kind of process which was used to make an antique fresco. On a layer, of raw plaster named "arriccio" (floating coat), there was applied a thinner layer of plaster, on which the artist sketched his drawing, and at last, a final layer of plaster ("intonachino" or "plaster finish") was applied, which was made of very thin mortar, and the latter was painted while it was still fresh. By the word "separation zone" or "detachment" in a fresco, we mean the lack of adherence of the floating coat to the underlying wall structure and/or to the plaster finish ("intonachino"), which gives rise, due to the permeability of the material, to air gaps whose shapes and dimensions vary considerably. In most cases, the reason for this is an excessive air humidity in the surroundings of the fresco. In the absence of adequate restoration work, fissures and complete separation of parts of the painted surface may occur. The technique most used by restorers, for the detection of separation zones in frescos, is an empiric and very invasive (destructive) one, called "hammer" technique, which amounts to hitting the fresco surface or wall structure surface while listening to the difference in the sound emitted by the same.

At an international level, the problems mentioned above concern the more general patrimony of mural paintings, which includes also works of art which are not antique.

Even if this problem seems not to be as important as in Italy, there are however European countries like France, Germany, Austria and Greece, in which the need to effect precise diagnoses on the frescos is as urgent as in Italy. Among nondestructive scientific techniques, the only one which currently is suited to give some information on the presence of separation zones in frescos, is the so-called "thermovision" (see Segal, Y., et al., Research Techniques in Nondestructive testing, Edit. R. S. Sharpe, Acad. Press, New York, 1977), which, however, often gives results which are difficult to construe. Moreover, its complex instruments is which are not easy to use and its very high cost, considerably limit the use of this technique.

Attempts aiming at providing -in this field- alternative techniques which could replace the thermovision, and in particular acoustic techniques, have not reached till now satisfying results. An example of these attempts is given by the "ecospectrographic" technique first presented in "Un progetto per Piero della Francesca" (Matteini M., et al., 1989, Indagini diagnostico-conoscitive per la conservazione della Leggenda della Vera Croce e della Madonna del Parto, Alinari, Firenze), but no positive results are known in this respect, neither for applications concerning specimens nor for those of real frescos.

A further and more recent technique, based on a vibrometer system measuring the frequency response function "acceleration/force" or inertance, seems to have reached some useful result on appropriate specimens under ideal laboratory isolation conditions, but experiments on real frescos have not yet been done (see Mannaioli A., 1992, Progetto e realizzazione di un sistema vibrometrico per l'identificazione di distacchi negli affreschi, Tesi di laurea, Fac. Ingegneria, Università "La Sapienza", Roina, 1991/1992). Actually, the two above mentioned acoustic techniques, leaving out of consideration the laboratory results which have been thereby obtained, have the serious limitation that they cannot be classified as nondestructive.

In fact, they require that the painting be physically "hit" by means of a mechanical source, in order to excite the structure to be analysed, and be "touched" by means of sensors responsible for the detection of the acoustic response.

For what concerns the technique employing a laser vibrometer, it has been noted that the same is very useful for studying the vibration modes of structures, due to the fact that it is totally independent from environmental noise, however, the actual research progress does not allow to use the sole modal analysis in order to discriminate in a univocal way the resonances of the separation zones from all possible vibrational modes of the excited structures comprising said separation zones.

DISCLOSURE OF INVENTION

The acoustic) technique suggested by the inventors is different from the above mentioned ones, with respect to the use of a different acoustic parameter (the acoustic energy absorption coefficient) as physical indicator of the separation zones, and moreover, with respect to a perfectly nondestructive method of analysis of the painting.

In fact, the acoustic source used to excite the surface, and the sensor detecting the acoustic signal reflected by the same, are both positioned at an apropriate distance from the fresco, without need to "touch" it, while using acoustic waves of limited amplitude. The new proposed method utilizes an appropriate signal processing system allowing to discriminate the feeble signals indicating the detachment zone, from the other noise.

Brief Description of Drawings

The present invention will now be explained for illustrative and non-limitative purposes, with reference to a particular embodiment thereof, which is shown in the drawings, wherein:

FIG. 4 is a plot of a sequence of nine real Cepstrum signals, which have been obtained by a mesurement scanning, along a vertical axis, on a wall comprising artificial separation zones;

FIG. 8 shows the map of the separation zones on the second of the three artificial mural structures realized in the laboratory, having a single circular central separation zone with a diameter of 30 cm;

FIG. 9 shows the map of the separation zones on the third of the three artificial mural structures produced in the laboratory, having a single circular central separation zone with a diameter of 39 cm.

Best Mode of Carrying out the Invention

Figure 1:
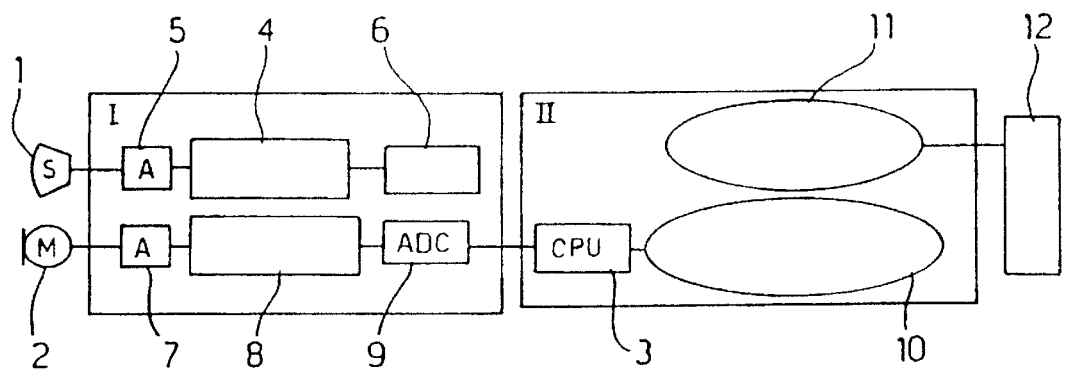
FIG. 1 is a schematical general representation of the device for the detection of separation zones in frescos, according to the present invention.

The method and the related device for carrying out the detection and the realization of the map of the separation zones, will be described with reference to the schematic general drawing of FIG. 1. The device includes two distinct parts: the acoustic wave trasmission/receiving unit (I), and a system (II) based on a microprocessor having a signal acquisition and signal processing task, for realizing the acoustic image of the separation zone.

The transmission/receiving unit comprises an acoustic source S, denoted by 1, which is tunable in appropriate frequency bands (see the following description and particularly FIG. 5) and a wideband detector, M, denoted by 2, which receives the acoustic signal reflected by the structure being analysed. The reflected acoustic signal is input in the CPU of the microprocessor, denoted by numeral 3, which adequately processes it according to a complex method based on a specific algorithm. This kind of processing allows to perfectly separate the faint signals indicating the sound absorption, from the background noise. The signals obtained in this way are further processed so as to permit the automatic recognition by the microprocessor, of the separation zones of the fresco. In this way it is possible to realize a map of said separation zones (FIGS. 6, 8, 9) by a direct correlation of the latter to the "acoustic images" of the absorption anomalies of the acoustic energy.

The impulsive acoustic source 1 generates an acoustic wave which is obtained by means of a wave generator 4, whose signal is amplified by the amplifier 5. Numeral 6 denotes a clock.

The signal of the wideband detector 2 is amplified by an amplifier 7, thereafter it is sent to a band-pass filter 8 and to the input of an analog-to-digital converter 9, and the latter transmits a digital signal to the CPU 3. Everything related to the hardware of the device is illustrated in FIG. 1 by rectangular blocks, whereas the software is denoted by corresponding oval parts. The part indicated by 10 is the so-called "detachment physical descriptor" which has a correlation with the acoustic energy absorption coefficient.

It allows to extract the relevant information from the various measurement signals and to visualize it on the display 12 by means of the imaging processor 11. The laboratory prototype of the device, used to carry out the new method, operates in the following manner. The acoustic source 1 transmitting the signal, and the receiver 2, are disposed along the same axis, perpendicularly to the surface of the painting being analyzed, on a support which is itself connected to an X-Y type frame (not shown); in this manner, it is possible to perform the scanning parallelly to said surface, along vertical and horizontal axes, using a small-sized electric motor (not shown).

The apparatus can electronically control the most adequate scanning method, and it can detect the individual positions occupied by the transceiver device, corresponding to the excited zones of the painting surface, moreover, it can simultaneously acquire the signal reflected by the latter. Preliminary tests may be performed on certain points of the painting surface, before effecting the very scanning. The measurement may be carried out at an appropriate distance from the painting surface, which is not necessarily fixed in advance, since the apparatus is calibrated in a way to normalize each measurement to a certain standard predetermined distance. Once the position of the zones on the painting giving rise to absorption have been approximately determined, a scanning along lines is performed, in accordance with the points making up a predetermined reticular pattern. In this manner it is possible to obtain a map of the separation zones present on the whole painting surface. The measurement of the absolute value of the absorption coefficient is relatively irrelevant, instead, one is interested in the variation of the latter with respect to its minimum value, which corresponds to a zone of the painting giving rise to a maximum value of reflection.

The microprocessor performs this comparison automatically, and the maximum value of the Cepstrum is used to normalize the absorption coefficients. The acoustic signal processing apparatus according to the present invention makes use of a method which is based on the so-called "Cepstrum" algorithm. The latter has been employed for the first time in 1963 (Bogert, B. P., Healy, M. J. R., and Tukey, J. W., in Proceedings of Symposium on Time Series Analysis by Rosenblatt, M., (Ed.), Wiley, N.Y. 1963, pages 209–243) and has been successfully applied to the field of underwater acoustics. The signal analysis by means of the Cepstrum is adopted in the present invention as a starting point for a treatment of the signal which allows the microprocessor to automatically recognize the separation zones in a fresco.

In the following, in order to stress the importance of the suggested innovative acoustic method as compared with the traditional method used for the determination of the acoustic absorption coefficient of solid structures, it will be appropriate to describe both of them.

Figure 2:
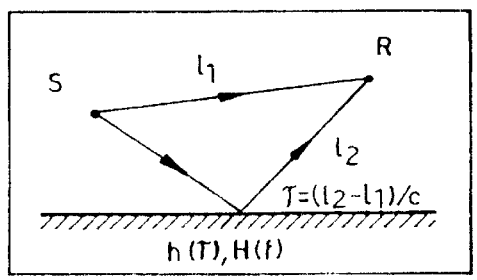
FIG. 2 is a schematic view illustrating the transmission and reception of an acoustic signal reflected by a reflector.

The preliminary approach to the structure to be analysed is the same for both methods. An impulsive acoustic source S is positioned at a certain distance from said surface, in such a way that the direct wave covers the distance $l_1$ and the reflected wave the distance $l_2$ before reaching the receiver R (see FIG. 2). The acoustic pressure signal p(t) which is received by the microphone, is the sum of the direct signal $p_d(t)$ and of the reflected signal modified by the surface, which is dampened due to the the greater distance to be covered and which is also delayed by the amount τ. In the time domain this signal may analytically be expressed as follows:

$$p(t)=p_d(t)+l_1/l_2 p_d(t)*h(t-\tau) \quad (1)$$

that is, it is the sum of the direct signal and the reflected signal, wherein the latter is obtainable through the convolution of the signal $p_d(t)$ "at the input" of the reflector, with the impulse response $h(t)$ of the reflector.

In the frequency domain, by applying the Fourier transform, formula (1) becomes $$P(f)=P_d(f)[1+l_1/l_2 H(f)e^{-i2\pi f\tau}] \quad (2)$$

After these introductory remarks, we can proceed with the description of the two-different methods. a) Conventional method relying on the preliminary measurement of the direct dignal, $p_d(t)$, and on that of the reflected signal $p_r(t)=p(t)-p_d(t)$ The preliminary measurement of the direct signal $p_d(t)$ (usually performed in an anechoic room), allows to obtain the reflected signal $p_r(t)$ by subtraction of $p_d(t)$ from the composite signal detected at the microphone.

Then, the Fourier transforms of $p_r(t)$ and $p_d(t)$ are calculated, thereby obtaining $p_r(f)$ and $p_d(f)$, and also the reflection coefficient $\rho(f)$ is computed, as the ratio of these two measurement values $$\rho(f)=P_r(f)/P_d(f) \quad (3)$$

At last, one obtains the coefficient of absorption, $\alpha(f)$, by means of the formula $$\alpha(f)=1-\rho(f) \quad (4)$$

b) Determination using the CEPSTRUM technique This method has the considerable advantage of allowing an in situ measurement of the absorption coefficient under the real environmental situation of the structure to be analyzed, even in presence of a superposition of the direct signal and the reflected one, and/or in presence of background noise. This cannot be done with the conventional method, since the latter requires a preliminary measurement of $p_d(t)$ inside an anechoic room, if useful results are to be obtained. While the measurement of the absorption coefficient $\alpha(f)$ according to the conventional method illustrated under the above paragraph (a), does not give rise to any kind of problem in case of an industrially manufactured article (e.g. a panel), which may be introduced in an anechoic room in order to perform the measurements, obviously, in case of a fresco, a method must be used which allows to extract the feeble reflection signal also in presence of noise and/or superposition of $p_d(t)$ and $p_r(t)$, as mentioned above.

According to the Cepstrum method, the power spectrum of the signal is calculated by squaring the absolute value of the above formula (2), and taking the natural logarithm thereof $$\ln|P(f)|^2=\ln|P_d(f)|^2+\ln[1+l_1/l_2 H(f)e^{-i2\pi f\tau}]+\ln[1+l_1/l_2 H^*(f)e^{+i2\pi f\tau}] \quad (5)$$

The last two terms of equation (5) may be expressed by the series expansion of the natural logarithm $$\ln(1+z)=z-z^2/2+z^3/3- \quad (6)$$

After substitution of this expression in the above formula (5), the inverse transform is calculated, thereby obtaining the so-called power Cepstrum $$C(t)=C_d(t)+l_1/l_2 h$$
$$(t-\tau)-l_1/l_2)^2 \frac{1}{2}h$$
$$(t-\tau)*h(t$$
$$-\tau)+\ldots+l_1/l_2 h$$
$$(-t-\tau)-(l_1/l_2)^2 \frac{1}{2}$$
$$h(-t-\tau)*h(-t$$
$$-\tau)+\ldots \quad (7)$$

In equation (7), $C(t)$ is the Cepstrum of the composite signal (direct signal plus reflected signal) and $C_d(t)$ is the Cepstrum of the direct signal. The following terms are the effect of the presence of the reflector on the signal received at the microphone. They appear at times $+\tau$, $-\tau$, $+2\tau$, $-2\tau$, etc.

The term which appears at time $+\tau$, leaving out the factor $l_1/l_2$, is the impulse response of the reflector. By comparison of relation (7) with relation (1), it obviously follows that the Cepstrum method simply transforms the effect produced by the reflector, from a convolution to a simple addition. If the determination of the Cepstrum is made in such a way that the term $h(t-\tau)$ may be easily distinguished from the other contributions of the signal, it may be extracted from the Cepstrum and its Fourier transform may be calculated in order to obtain $H(f)$, that is, the reflection coefficient of the reflector. Since the term containing $h(t-\tau)$ follows the term $C_c(t)$, it is desirable that the latter decays rapidly so as to become negligible in proximity of the time $\tau$. To this effect it is necessary to appropriately choose the signal of the source 1.

Figure 3:
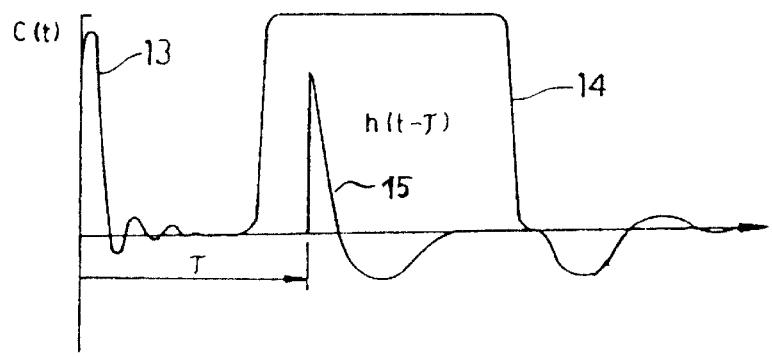
FIG. 3 shows an example of extraction of the impulse response h(t−τ) starting from the so-called "Cepstrum", C(t), of the signal.

FIG. 3 shows a simple schematic way of extracting the impulse response $h(t-\tau)$ starting from the Cepstrum, $C(t)$, Of the signal, whereas in FIG. 4 the real signals are plotted as a function of time, which have been obtained by performing a series of (nine) measurements on a test panel (wall) including artificial detachments, realized in the manner described later (see paragraph: tests performed on artificial frescos). Absorptions of the Cepstrum signal may be noted in the third trace (diagram) starting from the uppermost, and in the second and third trace, starting from the lowermost trace, all of which correspond to separation zones (detachments) Starting from signals of this kind, a program for the processing of the signal described hereinafter -, has been implemented in order to make the microprocessor automatically recognize the separation zones and the amount of their detachment.

For each position of the surface to be analyzed, an average is determined first on a certain number of determinations of the Cepstrum signal (each of them being represented by a trace of the kind shown in FIG. 4), and thereafter a software filter of the lowpass type is used to reduce the background noise. This improves the signal-to-noise ratio. Thereafter, a very narrow time window is applied around the average value of the peak $h(t-\tau)$, in order to extract the information about the intensity of the reflected signal contained therein (see FIG. 3). This method is applied to all points of the surface to be analyzed, and the obtained results are normalized both with respect to the maximum detected value off the Cepstrum, and to a predetermined distance of the transceiver device with respect to said surface.

Figure 6:
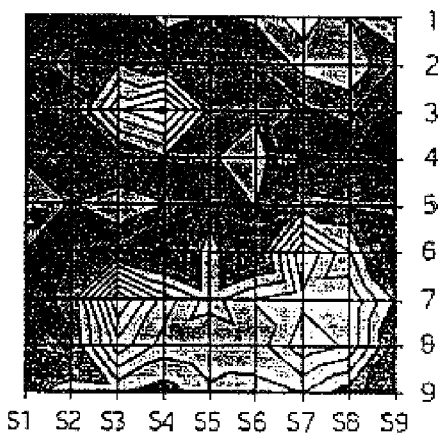
FIG. 6 is a map (bidimensional representation) of the separation zones, present on a first one of three mural structures prepared in the laboratory.

The results obtained in this way may be represented by a matrix (nxm) whose elements correspond to the value of the impulse response $h(t-\tau)$ at each point of the fresco. The information contained in this matrix is then processed by means of an image processing program in order to be visualized in the form of "acoustic images" of the relative value of the absorption, as shown in FIG. 6, FIG. 8 and FIG. 9. It should be noted that in FIG. 3 the numeral 13 denotes the Cepstrum of the direct signal ("direct Cepstrum"), the number 14 indicates the window function, and the curve 15 is the impulse response $h(t-\tau)$.

The information concerning the separation zone, which may be obtained by means of the device, is of two distinct types. The first kind of information relates to the average linear extension of the detachment, if the latter is considered to be a vibrating system as—for instance—a circular membrane fixed at its boundary, and this information is provided by the bidimensional absorption map of the type shown in FIGS. 6, 8, 9. The second kind of information relates to the height of the separation zone (detachment), that is the maximum value of the distance between the two interfaces of the air gap formed inside the detachment. This distance is related—provided other conditions remain the same—, to the resonance frequency for which the maximum value of the absorption is recorded, according to a relation of the type $f(x)=k/(x\propto)$, where $f(x)$ is the frequency, x is the height of the detachment, k and $\propto$ are parameters which depend on the velocity of sound in air, the air density, and from the thickness and density of the detached plaster mass.

The determination of the height of the separation zone or detachment requires an analysis of the signal in different frequency bands, for which the device repeats the same processing operations of the signal. It is therefore possible to obtain a plurality of maps, each of them corresponding to the dominant frequency characterizing the analyzed band. From a comparison of the maps, it is possible to obtain the relative value of the height of each detachment at the given frequency. The final result is a tridimensional map, which shows both the linear extension of the detachment, and its maximum relative height.

Figure 5:
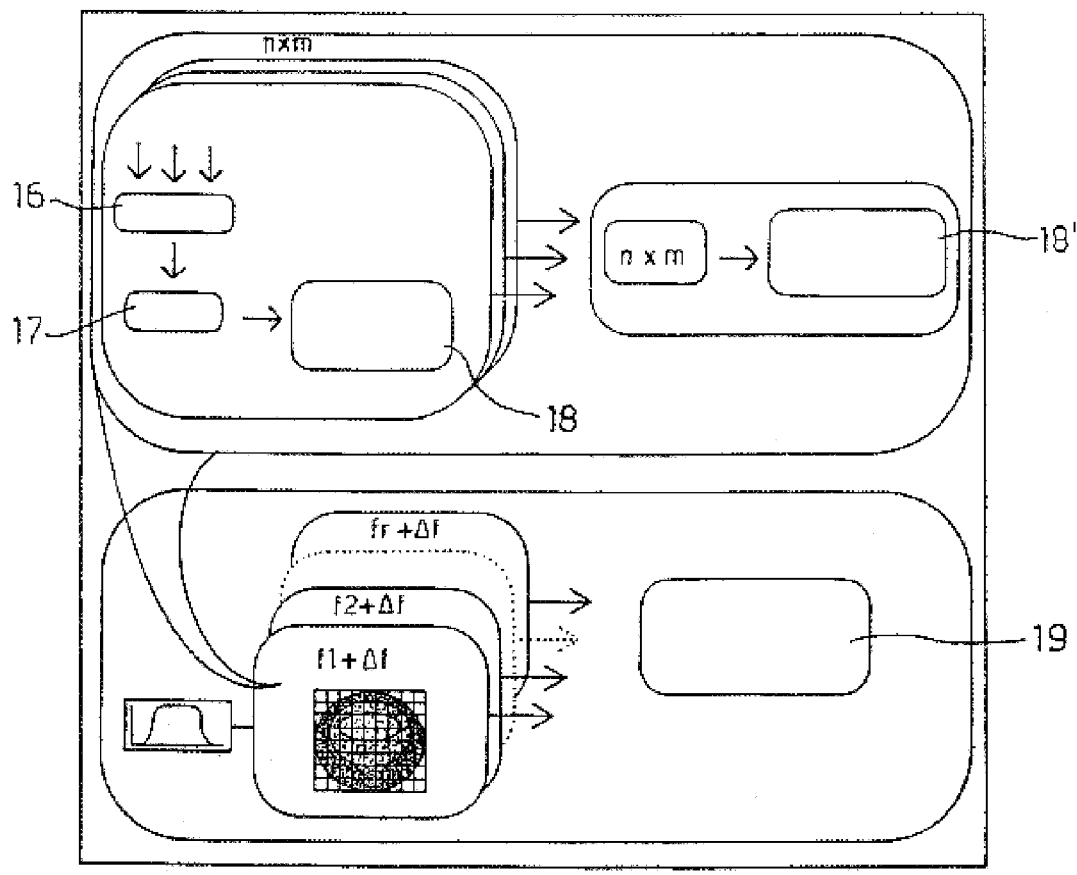
FIG. 5 is a general schematic illustration of the firmware inserted in the microprocessor of the device of the present invention, shown in FIG. 1, which is responsible for signal processing.

The latter corresponds to a well-defined frequency which is the detachment resonance frequency, giving rise to the maximum absorption of acoustic energy. A tridimensional map which is an exact representation of the detachments, has not been included in the drawings; the latter only show, by means of different color gradations (FIGS. 6, 8, 9) the heights and extensions of the detachments. FIG. 5 is a general schematic drawing of the firmware inserted in the microprocessor which performs the above described signal processing. The upper part of this figure schematically illustrates the procedure adopted to realize a single bidimensional map, which is repeated for each frequency band f1, f2, . . . , fr, as may be seen in the lower part of the same figure, where the final map of the detachments is constructed in three dimensions.

In FIG. 5, the three vertical arrows denote a certain number of measurements performed using the same signal of the source 1, the block 16 denotes the average of said signals (corresponding to a single point of the "reticular pattern"), block 17 denotes the above mentioned software filter, and block 18 denotes the determination of the peak intensity.

After having determined the matrix of nxm peak values, corresponding to the reticular pattern of the measurement points which had been previously selected on the fresco, a bidimensional map of the fresco—related to a single frequency—is visualized (block 18'). The tridimensional visualization of the map of the detachments occurs in block 19.

Tests Performed on Artificial Frescos

In order to show the goodness of the method suggested by the present invention, a series of experimental tests have been performed in the laboratory on detachment models having simple geometrical shapes, constructed from appropriate specimens with structural features similar to those of ancient frescos. Said artificial detachments have been realized on three different walls of equal area (1.08×1.00 m$^2$) made of terracotta bricks.

Each wall has been treated following the above mentioned process, which was used in times past before the execution of a fresco, that is, the application on the wall surface of a raw plaster ("arriccio") made of a mixture of sand, calcium hydrate, anhydrous gypsum, and manganese dioxide, in appropriate amounts. The specimens, manufactured by using the same ingredients, and prepared by the Laboratorio di Restauro dell' Opificio delle Pietre Dure di Firenze, have been attached on said walls by means of the same plaster composition, and thereafter a second layer of thinner mortar was applied ("intonachino") which covered the whole surface of the wall.

FIG. 6 shows the detachments map realized for the first of the three mural structures available in the laboratory. It shows the result of a plurality of determinations of the physical descriptor related to the acoustic energy absorption coefficient, which were performed by the acoustic device (while the receiver was positioned about 30 cm away from the analyzed surface), through scanning along axes parallel to the wall. Ten measurements have been effected along each line or axis, with a pitch of 10 cm, and at each measurement point five signal acquisitions have been made, taking then the average therefrom.

The latter value has been chosen as the physical detachment indicator, being related to the acoustic energy absorption coefficient. Thereby, a map was obtained of the absorption coefficient by employing a set of different gradations of grey colours, including an almost white colour to which the value 1 was assigned (maximum absoption), and the black colour corresponding to the value 0 (minimum absorption).

Figure 7:
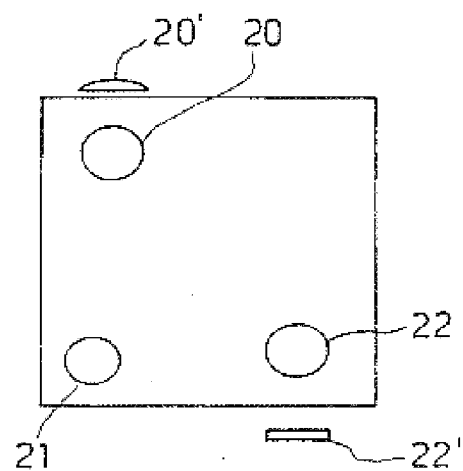
FIG. 7 shows the arrangement of the separation zones which were artificially prepared in the laboratory, together with their configuration, for the mural structure which gave rise to the map of FIG. 6.

FIG. 7 shows the positions and shapes of the specimens (separation zones or detachments) denoted by 20, 21, 22, which have been fixed in appropriate points on the first artificial wall in order to create said gaps. The numerals 20' and 22' denote the cross-sections of the specimens 20 and 22 respectively. By the same experimental procedure it has been possible to realize the detachments maps of the remaining two artificial structures (FIGS. 8 and 9), on which a respective single specimen—with a greater size than the preceding ones and with a respective diameter of 30 cm and 39 cm—was positioned at the center.

It may be observed that in all of said three structures the maximum absorption occurs in the detachment or separation zone, even if the distribution of the gradation of grey colour is not uniform, particularly in the neighbourhood of the edges. This is most likely due to a non perfect adherence of the specimen edges, which may already be present at the time of the laying of the (artificial) detachment, or be a consequence of local climatic factors, like humidity or temperature, inducing a separation of the specimen along part of its connecting edge. This latter drawback has certainly occurred for the structure with the 39 cm detachment (FIG. 9), which was exposed to the inclemency of the weather. Moreover, the discrete and relatively coarse (wide) scanning pitch, used for the reticular measurement pattern in this first set of tests, has restricted the resolution of the device, however, the latter may be increased by appropriately increasing the number of determinations for each scanning line. Account should also be taken of the fact that at the mural structure edges the measurement becomes difficult, because of the discontinuity existing in proximity of the brick-air interface, which normally is absent in real-life frescos.

An attempt has also been made to detect the detachment by using the laser vibrometer, under the same experimental conditions, that is by exciting the surface with the same acoustic source as before, and with the same intensity, and analyzing the vibrational modes at the, site of the separation zones (detachments), but no useful results were obtained in this way.

Industrial Applicability

The experimental results obtained with the new method, on artificial detachments, allow to draw the following conclusions.

The specimens simulating the detachments behave like elastic diaphragms or membranes capable of vibrating according to certain vibration modes, and to absorb, for certain frequencies, part of the acoustic energy impinging thereon. The acoustic energy absorption coefficient has revealed himself to be "the physical indicator" which is most appropriate for the detection of the detachment. The device proposed by the invention is suited to perform, in situ, on real-life frescos, a detection and a map of the detachments.

Obviously the present invention should not be interpreted by limiting it to the illustrative realization described above.

It is clear, for instance, that measurements could also be effected on a plurality of points of the fresco, which do not form an "array" nxm.

Moreover, it would be possible also to use the above method to effect measurements on any kind of reflected signals, that is, not only those obtained by placing the source 1 and the detector 2 on the same line or axis perpendicular to the fresco.

It has been said that the measurements may be done by using a device support which is connected to an X-Y frame.

However, in case of a non-planar surface of the fresco bearing wall, the disclosed method is also applicable by replacing the X-Y frame with an adequate movable scanning support.

The measurement results obtained with the present device, may be stored and visualized on the display in a later period.

It may thus be seen that the invention is susceptible of many possible variants, all comprised in the same inventive concept.

The present invention could be used as well to reveal gaps in "bidimensional" structures consisting of several thin layers capable of "detaching", without being limited to the application of mural paintings.

The acoustic source S may also emit a wideband signal including all possible frequencies which are useful to excite separation zones of any linear dimension and height whatever. In this case, instead of carrying out several scanning operations, each time for a different frequency band, a single scanning operation will be enough, and the microprocessor will then obtain therefrom the data for the spectral analysis, according is to the aforesaid bands fl, . . . , fr.

What is claimed is:

1. A nondestructive acoustic method for the detection of separation zones in stratified structures and particularly in frescos and mural paintings, and for the realization of bidimensional or tridimensional maps of said separation zones or "detachments", characterized in that it uses as detachment physical indicator the acoustic absorption coefficient obtained from the value of the direct signal $p_d(t)$ of the impulsive acoustic source, which may emit an acoustic wave of appropriately large bandwidth, so as to excite detachments of any dimension, and from the detected signal value at a detector p(t); wherein, said impulsive acoustic source and the detector are both located at a specified distance from the structure to be analyzed, and the separation of the direct signal $p_d(t)$ of the source from the reflected signal $p_r(t)$ is obtained by employing the Cepstrum technique, wherein for each point of a plurality of measurement points, an average is taken on a certain number of Cepstrum signal determinations, and thereafter a software filter is used to reduce the background noise, and subsequently a very narrow time window is applied around the average value of the peak h(t−τ) produced by the reflection onto the respective measurement point, so as to extract the relevant information about the intensity of the reflected signal; the obtained results being then normalized with respect to the maximum value of the detected Cepstrum signals, and being used to form a set of characteristic values of the absorption at a specified frequency which are useful to determine the extension of said separation zones.

2. A nondestructive acoustic method according to claim 1, wherein the obtained results are automatically normalized with respect to the distance from the structure being analyzed, so as to render the same independent from the position of the detector and the source.

3. A nondestructive acoustic method according to claim 1, wherein the set of measurement points is the intersection of a reticular pattern of mutually orthogonal lines, in such a way that the result of the measurement is represented by a matrix of nxm values or elements.

4. A nondestructive acoustic method according to claim 1, wherein said set of values or matrix is used by an image processing program, in order to form acoustic images of the relative absorption which represent the bidimensional extension of the detachments.

5. A nondestructive acoustic method according to claim 1, wherein the source is tuned on several frequency bands, and the aforesaid set of values is determined for each dominant frequency, and from a comparison of said sets of values the tridimensional detachment map is obtained, which gives the maximum height of the detachment for each measurement point.

6. A nondestructive acoustic method according to claim 1, wherein the processing of the signal p(t), that is the determination of the Cepstrum signal C(t) and all of the following operations, is performed by a firmware which is inserted in a microprocessor.

7. A device for the nondestructive acoustic detection of separation zones in stratified structures, frescos and mural paintings, and for the realization of bidimensional or tridimensional maps of said separation zones comprising a first part for the transmission and reception of acoustical waves using as detachment physical indicator an acoustic absorption coefficient obtained from a value of a direct signal $p_d(t)$ of an impulsive acoustic source which emits an acoustic wave of appropriately large bandwidth so as to excite detachments of any dimension, and from a detected signal value at a detector p(t) included in the first part, the impulsive acoustic source and the detector being both adapted to be located at a specified distance from the structure to be analyzed, a second part including a microprocessor for the acquisition and processing of received signals, by separation of the direct signal $p_d(t)$ of the source from the reflected signal $p_r(t)$, obtained by employing the Cepstrum technique so that for each point of a plurality of measurement points, an average can be taken on a certain number of Cepstrum signal determinations, and a software filter for thereafter reducing background noise, and subsequently applying a very narrow time window around the average value of the peak h(t−τ) produced by reflection onto the respective measurement points, so as to extract the relevant information about the intensity of the reflected signal, the microprocessor being adapted to normalize the obtained results with respect to a maximum value of the detected Cepstrum signals to form a set of characteristic values of the absorption at a specified frequency which are useful to determine the extension of said separation zones.

8. A device according to claim 7, wherein the acoustic source and the detector are mounted on a frame allowing a scanning in two directions X-Y of the structure to be analyzed, said detector and said acoustic source being further disposed along the same axis orthogonal to the structure surface.

9. A device according to claim 8, wherein after some preliminary measurements the scanning method which is judged to be the most appropriate is controlled electronically, by detecting each time the position is occupied by the source and the detector, and by simultaneously performing the acquisition of the reflected signal.

10. A device according to claim 7, including a display unit for displaying bidimensional and tridimensional maps of acoustic images.

* * * * *